(12) United States Patent
Amit et al.

(10) Patent No.: US 11,006,860 B1
(45) Date of Patent: May 18, 2021

(54) METHOD AND APPARATUS FOR GAIT ANALYSIS

(71) Applicant: Motionize Israel Ltd., Tel Aviv-Jaffa (IL)

(72) Inventors: Eran Amit, Pardes Hanna-Karkur (IL); Shai Rosenblit, Beit Yehoshua (IL); Amir Zviran, Tel Aviv-Jaffa (IL); Steve Barrett, Hull (GB); Moran Gad, Sde Yoav (IL)

(73) Assignee: MOTIONIZE ISRAEL LTD., Tel Aviv-Jaffa (IL)

( * ) Notice: Subject to any disclaimer, the term of this patent is extended or adjusted under 35 U.S.C. 154(b) by 0 days.

(21) Appl. No.: 17/063,132

(22) Filed: Oct. 5, 2020

Related U.S. Application Data (60) Provisional application No. 63/039,495, filed on Jun. 16, 2020.

(51) Int. Cl.
*A61B 5/11* (2006.01)
*G16H 40/67* (2018.01)
(Continued)

(52) U.S. Cl.
CPC ............ *A61B 5/112* (2013.01); *A43B 3/0005* (2013.01); *A61B 5/1117* (2013.01);
(Continued)

(58) Field of Classification Search
CPC ..... A61B 5/112; A61B 5/1117; A61B 5/6807; A61B 5/7267; A61B 5/7275;
(Continued)

(56) References Cited

U.S. PATENT DOCUMENTS

2008/0018066 A1   1/2008   Pickford
2008/0185799 A1   8/2008   Weisiger
(Continued)

FOREIGN PATENT DOCUMENTS

CN   201790034 U   4/2011
CN   103442607 A   12/2013
(Continued)

OTHER PUBLICATIONS

Clark et al., (2017) A general relationship links gait mechanics and running ground reaction forces. Journal of Experimental Biology 220: 247-258 with supplementary information.
(Continued)

*Primary Examiner* — Patrick Fernandes
(74) *Attorney, Agent, or Firm* — The Roy Gross Law Firm, LLC; Roy Gross (57) ABSTRACT

A computerized method performed by a processor, and computer program product the method comprising: receiving sensory data of motion by a human subject, the sensory data obtained during motion in an uncontrolled environment; extracting features from the sensory data; identifying a plurality of strides from the features extracted from the sensory data; calculating kinematic parameters of each stride from the plurality of strides from the sensory data; classifying each stride from the plurality of strides in accordance with the kinematic parameters to obtain a stride type; and outputting the stride type for the plurality of strides.

21 Claims, 8 Drawing Sheets

(51) Int. Cl.
*G16H 50/20* (2018.01)
*G16H 50/70* (2018.01)
*G16H 10/60* (2018.01)
*A43B 3/00* (2006.01)
*G16H 40/40* (2018.01)
*A61B 5/00* (2006.01)
*G16H 50/30* (2018.01)

(52) U.S. Cl.
CPC .......... *A61B 5/6807* (2013.01); *A61B 5/7267* (2013.01); *A61B 5/7275* (2013.01); *G16H 10/60* (2018.01); *G16H 40/40* (2018.01); *G16H 40/67* (2018.01); *G16H 50/20* (2018.01); *G16H 50/30* (2018.01); *G16H 50/70* (2018.01)

(58) Field of Classification Search
CPC ...... A61B 5/7271; G16H 40/67; G16H 50/30; G16H 50/70; G16H 50/20; G16H 40/40; G16G 10/60; A43B 3/0005
See application file for complete search history.

(56) References Cited

U.S. PATENT DOCUMENTS

| | | | | |
|---|---|---|---|---|
| 2010/0184563 | A1* | 7/2010 | Molyneux | A43B 5/02 |
| | | | | 482/1 |
| 2010/0305480 | A1* | 12/2010 | Fu | A61B 5/1121 |
| | | | | 600/595 |
| 2011/0054359 | A1 | 3/2011 | Sazonov | |
| 2011/0066383 | A1* | 3/2011 | Jangle | G06K 9/00342 |
| | | | | 702/19 |
| 2013/0123665 | A1* | 5/2013 | Mariani | A61B 5/1038 |
| | | | | 600/592 |
| 2013/0244211 | A1* | 9/2013 | Dowling | G16H 20/30 |
| | | | | 434/247 |
| 2015/0359457 | A1 | 12/2015 | Blumenthal | |
| 2016/0262687 | A1* | 9/2016 | Vaidyanathan | A61B 5/1123 |
| 2016/0309834 | A1 | 10/2016 | Zwick | |
| 2020/0229762 | A1 | 7/2020 | Gad | |

FOREIGN PATENT DOCUMENTS

| | | |
|---|---|---|
| CN | 105229664 A | 1/2016 |
| CN | 105453090 A | 3/2016 |
| EP | 3086320 A1 | 10/2016 |
| EP | 3092913 A1 | 11/2016 |
| EP | 3104290 A1 | 12/2016 |
| TW | 201515636 A | 5/2015 |
| WO | 03000355 A1 | 1/2003 |
| WO | 2014066779 A2 | 5/2014 |
| WO | 2015164944 A1 | 11/2015 |
| WO | 2016037879 A1 | 3/2016 |

OTHER PUBLICATIONS

Nguyen et al., (2015) Dynamic Human Gait Phase Detection Algorithm. The ISSAT International Conference on Modeling of Complex Systems and Environments (MCSE) Jun. 8-10, 2015, Da Nang, Vietnam. 5 pages.

MPU-9150™; Product Specification. Release Date: Sep. 18, 2013 (Sep. 18, 2013). InvenSense Inc. Sunnyvale, CA, USA. Retrieved from: https://invensense.tdk.com/wp-content/uploads/2015/02/MPU-9150-Datasheet.pdf, 50 pages.

\* cited by examiner

| Test on train confusion matrix | Forward_Walk | Turn_Walk | Forward_Run | Backward_Run | Turn_Run | Turn_Leap | Recall |
|---|---|---|---|---|---|---|---|
| Forward_Walk | 701 | 24 | 26 | 1 | 5 | 2 | 92% |
| Turn_Walk | 104 | 236 | 55 | 3 | 6 | 4 | 58% |
| Forward_Run | 11 | 1 | | 4 | 5 | 8 | 97% |
| Backward_Run | 2 | 1 | 11 | 93 | 3 | 3 | 82% |
| Turn_Run | 11 | 6 | 155 | 4 | 115 | 6 | 39% |
| Turn_Leap | 2 | 4 | 24 | 1 | 3 | 334 | 91% |
| Precision | 84% | 87% | 77% | 88% | 84% | 94% | |

METHOD AND APPARATUS FOR GAIT ANALYSIS

CROSS-REFERENCE TO RELATED APPLICATION

This application claims the benefit of U.S. Provisional Application No. 63/039,495 filed Jun. 16, 2020, titled "Motion Type Classification to Improve Gait Dynamics Monitoring", hereby incorporated by reference in its entirety.

TECHNICAL FIELD OF THE INVENTION

The present disclosure relates to obtaining kinetic parameters of human motion in uncontrolled environment.

BACKGROUND OF THE INVENTION

Gait analysis is the systematic study of animal locomotion, and in particular the study of human motion. Gait analysis may be used to assess and treat posture-related or movement-related problems in individuals with conditions or injuries affecting their ability to perform certain activities, such as walking, turning, jumping, etc. Gait analysis is also commonly used in sports biomechanics, for helping sportsmen perform their activities better, more efficiently and avoid injuries. Gait analysis generally uses the views and professional observations of the observers, augmented by instrumentation for measuring body movements, body mechanics, and muscle activity of the muscles.

Gait analysis may encompass quantification, e.g., introduction and analysis of measurable physiological and biomechanical parameters; interpretation, i.e. drawing various conclusions about the condition and the motion of the subject, e.g., health, age, size, weight, speed etc. from the measured values and patterns; and making recommendations or taking corrective actions, such as training certain motions, improving the motions, reducing injuries, or the like.

Inertial measurement units (IMU) placed on a user's body provide information about the kinematics, e.g., positions, velocities and accelerations. Traditionally, the analysis is based on kinetic measurements obtained in controlled environments, such as a designated laboratory where the data is collected while the subject is performing pre-defined activities on stationary equipment.

SUMMARY OF THE INVENTION

One exemplary embodiment of the disclosed subject matter is a computer-implemented method comprising: receiving sensory data of motion by a human subject, the sensory data obtained during motion in an uncontrolled environment; extracting features from the sensory data; identifying a plurality of strides from the features extracted from the sensory data; calculating kinematic parameters of each stride from the plurality of strides from the sensory data; classifying each stride from the plurality of strides in accordance with the kinematic parameters to obtain a stride type; and outputting the stride type for the plurality of strides. The method can further comprise: providing the kinematic parameters to a model associating kinematic parameters and kinetic parameters for the type of gait, for obtaining kinetic forces applied on and by the subject in response to performing gaits having the kinematic parameters; and outputting the kinetic parameters. The method can further comprise: calculating advanced kinetic parameters for a plurality of strides; and outputting the advanced kinetic parameters. Within the method, a feature from the features is optionally selected from the group consisting of: human subject information including: subject height, weight, age, gender, leg length, foot length, or dominant leg; stride information for each stride in a sequence of one or more strides including: side, stride length, stride duration, contact time with the ground, flight ratio, stride change in heading angle, pronation, maximal foot height, or change in height; and ball touch data, including: type or release velocity. Within the method, a feature from the features optionally relates to the sensor raw data in one or more dimensions in time or frequency domain. Within the method, a feature from the features optionally relates to a three dimensional motion profile of the human subject. The method can further comprise combining the model with an analytic model, for determining effective kinematic states in the uncontrolled environment to fit to controlled environment states. The method can further comprise combining the model with an analytic model, for interpolating kinematic gait properties as a function of foot velocity. Within the method, the sensory data is optionally obtained from one or more sensors mounted on one or more shoes of the human subject. Within the method, the sensory data is optionally obtained from one or more sensors mounted on one or more shoes of the subject and an additional sensor mounted on another location on the human subject. Within the method, the sensory data is optionally obtained from one or more sensors comprising one or more Inertial Measurement Units (IMU) or one or more motion capture systems. The method is optionally used for assessing a medical condition of the human subject. The method can further comprise providing an indication to an increased risk of fall or another neurological condition of the human subject based on changes in kinetic and kinematic parameters or recognition of abnormal gait patterns.

Another exemplary embodiment of the disclosed subject matter is a computerized method performed by a processor, comprising: receiving sensory data of motion by a human subject, the sensory data obtained during motion in an uncontrolled environment; extracting features from the sensory data; identifying a plurality of strides from the features extracted from the sensory data; and training a classifier upon the features, the classifier adapted to classify further sensory data into one of a plurality of gait types. Within the method, the classifier is optionally trained upon the sensory data using supervised training, wherein each of the plurality of strides is labeled in accordance with a gait type from the plurality of gait types. Within the method, the classifier is optionally trained upon the sensory data using unsupervised training. Within the method the classifier is optionally trained upon and classifies motion segments. Within the method, a feature from the features is optionally selected from the group consisting of: human subject information including: subject height, weight, age, gender, leg length, foot length, or dominant leg; stride information for each stride in a sequence of one or more strides including: side, stride length, stride duration, contact time with the ground, flight ratio, stride change in heading angle, pronation, maximal foot height, change in height; and ball touch data, including: type or release velocity. Within the method, the sensory data is optionally obtained from at least one sensor mounted on at least one shoe of the human subject.

Yet another exemplary embodiment of the disclosed subject matter is a computerized method performed by a processor, comprising: receiving calibration measurements for a gait type, the calibration measurements providing estimations of kinetic parameters applied by a person performing actions associated with kinematic measurements; receiving training sensory data comprising training kinematic parameters acquired from a human subject performing multiplicity of gaits of the type of gait, the training sensory data obtained during motion in an uncontrolled environment; extracting training features from the training sensory data; and generating a model providing an estimation of kinetic parameters in response to inputting sensory data obtained during performance of a gait of the gait type. Within the method, the calibration measurements are optionally obtained from a device used by users in a controlled environment. Within the method, the calibration measurements optionally comprise measurement data for discrete values of kinematic parameters. The method can further comprise receiving a semi empirical model associating the training kinematic parameters with training kinetic parameters. Within the method, the model is optionally further adapted to provide an estimation of kinetic parameters of a motion segment by the subject. Within the method, the relevant strides and relevant kinetic parameters are optionally selected based on frequency or severance. Within the method, the model is optionally also based on at least one analytic kinetic model.

Yet another exemplary embodiment of the disclosed subject matter is a computer program product comprising a computer readable storage medium retaining program instructions, which program instructions when read by a processor, cause the processor to perform a method comprising: receiving sensory data of motion by a human subject, the sensory data obtained during motion in an uncontrolled environment; extracting features from the sensory data; identifying a plurality of strides from the features extracted from the sensory data; calculating kinematic parameters of each stride from the plurality of strides from the sensory data; classifying each stride from the plurality of strides in accordance with the kinematic parameters to obtain a stride type; and outputting the stride type for the plurality of strides.

BRIEF DESCRIPTION OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION OF THE INVENTION

In the description below, unless noted otherwise, the term "gait" is to be widely construed as covering a pattern of movement of the limbs of animals, including humans, during locomotion over a solid substrate. The pattern may relate to a single stride or step, or to a plurality thereof.

In the description below, unless noted otherwise, the term "stride" is to be widely construed as covering the movement of one foot during a double step, i.e., from the time the heel of one foot contacts the ground, until the same heel contacts the ground again.

In the description below, unless noted otherwise, the term "step" is to be widely construed as covering a single step, for example from the time one heel forms contact with the ground, until the second heel forms contact with the ground.

Gait analysis is the study of motion, and in particular human motion, and is used to assess and treat individuals with conditions limiting their physical abilities, as well as sportsmen who are always in pursuit of improving their abilities. Gait analysis may use instrumentation for measuring body movements, body mechanics, and muscle activity of the muscles.

Traditionally, analysis is based on measurements obtained from sensors such as IMUS worn by the subject, and direct or indirect force measurement equipment, wherein the subject is performing pre-defined activities on stationary equipment in controlled environments, such as a designated laboratory.

One technical problem addressed by the disclosure is that a motion performed in a controlled environment is inherently different from a spontaneous motion, as would be performed under uncontrolled circumstances, such as within a game field, during a game, on a real jogging track rather than a treadmill, or the like. A controlled motion tends to be more expected and cautious, less likely to put extraneous efforts on the body, and generally unrepresentative of the actual motion.

Another technical problem addressed by the disclosure is that the extraction of kinetic parameters, e.g., forces acting on or by different parts of the body based on IMU measurement, is very limited. A significant limitation is that the currently existing analytical models are insufficient for calculating the kinetic parameters from the available kinematic parameters.

One approach for overcoming this limitation is reporting only about exceptionally high parameter values, which represent the biomechanical parameters, for example considering only "high intensity actions", wherein all other intensities are assumed to have negligible effect on the total athlete load. Moreover, in such approach, all "high intensity actions" are usually considered to have the same rank/load and thus their statistics in a simple count of all events. Thus, this approach, which is qualitative rather than quantitative, and is often used by sport scientists, uses the little information available and accordingly provides limited results.

Another approach for overcoming this limitation comprises training machine learning models based on IMU measurements taken in controlled environments, together with calibration data. Calibration data may relate to discrete data points which provide the forces applied by or to the human in relation with a certain collection or sequence of IMU measurements taken at one or more points of the subject body. However, in order to provide an effective model, a significant amount of data is required for extracting a plurality of parameters for each of a plurality of predetermined gait types. Therefore, generating a model representative of the large amount of data is unrealistic for extracting kinetic parameters of real-life uncontrolled events.

One technical solution of the disclosure relates to creating and using a classifier for determining a gait type upon kinematic parameters of uncontrolled motion. Determining gait type may provide for collecting person-wise or group-wise statistics of gait types, such as for individual players and sports teams. Such statistics may enable a coach, a sport scientist, a physician or even the player(s) to better assess and improve the personal and team coaching, reduce injuries, or the like. It will be appreciated that an existing classifier may be improved over time using unsupervised classification of further entries in a gait database.

Another technical solution of the disclosure relates to providing the kinematic parameters of gaits of a specific gait type collected during an uncontrolled motion of a subject, to a model constructed upon the specific gait type. The model is adapted to provide the kinetic parameters upon the kinematic parameters, thus providing insights to the mechanics of the gait, and enabling the subject to further improve the effectivity and/or efficiency of the gait performance, to avoid or reduce injuries, to adapt to existing injuries or limitations, or the like. In some embodiments, semi-empirical relations within the kinematic parameters can be found and used to describe the subject's condition. Such semi-empirical relations may make the created model simpler and make it more efficient and effective. Additionally or alternatively, the kinetic parameters may be calculated for a motion segment comprising a plurality of strides rather than for a single stride, compared over time, or the like.

One technical effect of the disclosure is the creation and usage of a classifier for classification of gaits according to the kinematic parameters into a plurality of gait types. The classification enables the collection of gait type statistics for a single subject or a group of subjects. Correctly classifying the gaits enables for using a separate kinetic model for each gait type, which is simpler and more efficient than a model related to a multiplicity of gait types.

Another technical effect of the disclosure is the ability to obtain kinetic parameters of motions in uncontrolled environments. Using existing technologies, such information could only be obtained in controlled environment, which suffers from limited variability of the motions, and inauthentic motions which are unrepresentative of real life motions. This effect is enabled by the creation of a model for assessing the kinetic parameters upon kinematic parameters of a gait, per a specific gait type. Such models can be created since the amount of data required for determining an independent model for each gait type is significantly smaller than the amount required for a plurality of gait types, and each such model in itself is much simpler. Further, the complexity of each gait type model can depend on the level of interest in this type. For example, a richer, larger or more detailed model may be created for gait types which are of higher importance then for models of lesser importance. Moreover, such models are usable due to the ability to classify gaits into types as detailed above.

Yet another technical effect of the disclosure is the ability to combine the kinetic parameters of consecutive gaits, in order to obtain the parameters of a full segment, and thus generalize the analysis for the full segment or motion by the subject. For example, information from multiple gaits may be combined to describe segment characteristic rather than stride characteristic. The segment characteristics may be further generalized into a user level characteristic, such as specific injury risk or other medical conditions and may be used for improving certain motions.

Figure 1A:
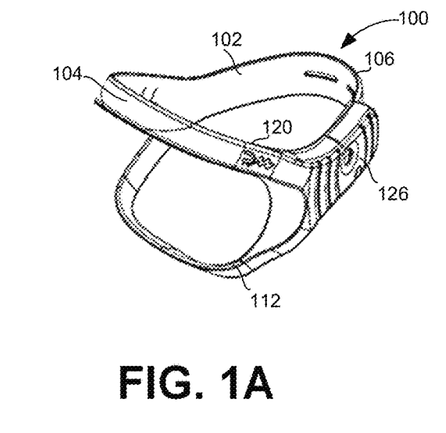
FIGS. 1A and 1B show two views of a footwear sensor unit, in accordance with some exemplary embodiments of the disclosed subject matter.
Figure 1B:
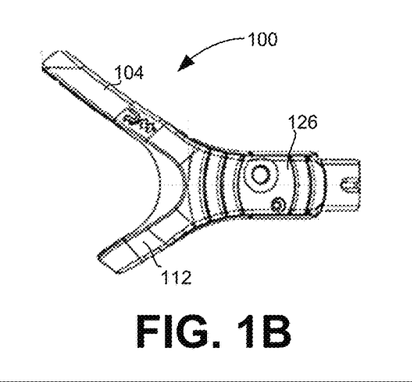
Figure 1C:
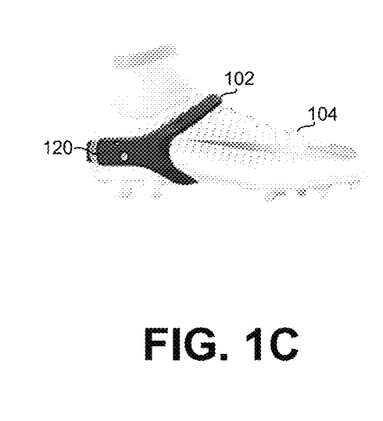
FIG. 1C shows a shoe having mounted thereon the footwear sensor unit, in accordance with some exemplary embodiments of the disclosed subject matter.
Figures 1D, 1E, 1F:
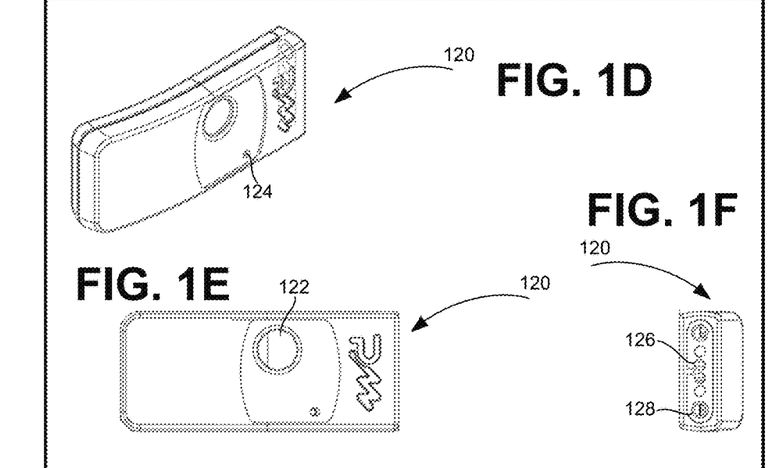
FIGS. 1D-1F show an exemplary housing for a motion sensor, in accordance with some exemplary embodiments of the disclosed subject matter.

Referring now to FIGS. 1A and 1B showing two views of a footwear sensor unit 100, and to FIG. 1C, showing a shoe 104 having mounted thereon the footwear sensor unit 100, and to FIGS. 1D-1F showing exemplary housing or casing for a motion sensor to be mounted on a shoe.

FIG. 1C depicts a footwear sensor unit 100 mounted on a shoe 104. Footwear sensor unit 100 includes a motion sensor module within a housing 120 and a mounting strap 102. Housing 120 and mounting strap 102 are alternatively referred to herein as a mounting system. Housing 120 may be made plastic, while mounting strap 102 may be elastic. Housing 120 may encase a motion sensor, such as a 6 degrees of freedom (DOF) motion sensor, for example an MPU-9150™ made by InvenSense headquartered in San Jose, Calif., USA. The product specification of the MPU-9150™ is incorporated by reference in its entirety and for any purpose. It will be appreciated, however, that the MPU-9150™ is merely an exemplary IMU and that any 6- or 9-DOF or other similar motion sensor can be used. In some embodiments, the motion sensor is a 9-DOF motion sensor of which the system only utilizes sensor data from a 3-axis gyroscope and a 3-axis accelerometer, i.e., only 6-DOF.

In some embodiments, sensory data may be obtained from a motion capture system, such as a camera, a video camera, or the like.

Housing 120 may be inserted into a compartment on elastic strap 102. Strap 102 may be mounted on soccer shoe 104.

Strap 102 may be made of any resilient, flexible and elastic material that can be stretched and flexed into place on shoe 104 and withstand the rigors of running, kicking a ball, contact with other players, or the like, while remaining securely in place and not snapping. Strap 102 and housing 120 may be made of rugged, heavy-duty material that is needed to withstand the constant rubbing against the ground (under-strap) and numerous impacts from the soccer ball and other objects such as other players' feet.

Housing 120 may comprise a sensor board, e.g., a printed circuit board (PCB) with components such as the IMU and electronic components. Housing 120 may be designed to keep the PCB safe from any impact it might endure during a match or a training session. Furthermore, the design of strap 102 may place housing 120 in a "ball-free shoe zone", where the ball is least likely to hit housing 120. Thus, housing 120 may be mounted such that it does not interfere with the way the ball is kicked on one hand, and is not damaged on the other hand. Moreover, strap 102 may be designed in such a manner that all foot movement is directly transferred to the motion sensor as if the foot and the sensor unit formed a single body.

FIGS. 1A and 1B illustrate an exemplary mounting strap 102. Mounting strap 102 may be formed as a single piece of material that includes a back-strap 106, an upper strap 104 and a lower strap 112. Back strap 106 may be U-shaped where the open ends of the U split into upper strap 104 and lower strap 112, both of which make closed circuits of their own. Back strap 106 is adapted to be fitted around the heel of a boot while the front on the boot slips between the upper strap 104 and lower strap 112. Upper strap 104 is adapted to lie across the top rim or near the top rim of the upper of the shoe where the shoe covers the foot, and to cover the part of the shoelaces near the tongue of the shoe. Lower strap 112 may be adapted to be fitted under the bottom of the shoe and to traverse the sole of the boot across an area of the sole which is devoid of cleats (studs). The design, flexibility and elasticity of the mounting strap ensure that the strap in held tightly in place, without shifting position. In embodiments, the strap is adjustable and may or may not form a closed circuit, i.e. two ends of the strap may be open. In other embodiments, the strap is not adjustable. Straps may come in different sizes and can be matched to a given shoe size. The straps can include some or all of the elements described above.

Both right- and left-hand mounting straps may be provided. For a right shoe, the mounting strap may include a holding pouch 126 on the right-hand prong of the U of back strap 106 as viewed from behind the strap and above. For a left foot shoe, holding pouch 126 may be located on the left prong of the U when viewed as above.

FIGS. 1D, 1E and 1F illustrate an exemplary housing 120 for motion sensor 100. Housing 120 may be removably insertable into pouch 126 of strap 102. In the depicted embodiment, housing 100 may include a button aperture 122 via which an operator can actuate the button that activate the motion sensor unit. The casing may further comprise an opening 124 through which one or more LED indicators can be seen. The lights may indicate the status of the motion sensor unit. Other embodiments of the housing may or may not include the same or similar apertures and may or may not have alternative or additional apertures and/or structural elements.

In the depicted embodiment, housing 120 may further include power contacts/ports and/or data ports 128. For example, ports 128 may be power ports for charging a rechargeable battery of the sensor unit and contacts 126 may be data ports for transferring raw or calculated sensor data via a physical medium. Alternatively, ports 128 may be used for data transfer while contacts 126 may be used for charging the unit. In other embodiments, one or more apertures within housing 120 may be used for securing the housing in place while the battery draws charge via contacts 126. The foregoing configurations are merely exemplary and it is made clear that any configuration for charging and/or transferring data is included within the scope of the invention.

Further details of the structure and operation of sensor unit 100 are provided in US Patent Application Publication no. US2020/0229762 published Jul. 23, 2020. In the following description, it is assumed that data has been collected and stored on a server.

It will be appreciated that the disclosed mounting straps and housing are example only, and that the sensors(s) may be installed anywhere, for example within the shoe sole, on another part of the shoe, as part of another garment such as a sock, or on another part of the user's body, such as the head, hand, torso, lower back, thighs, calves, or the like.

Figure 2:
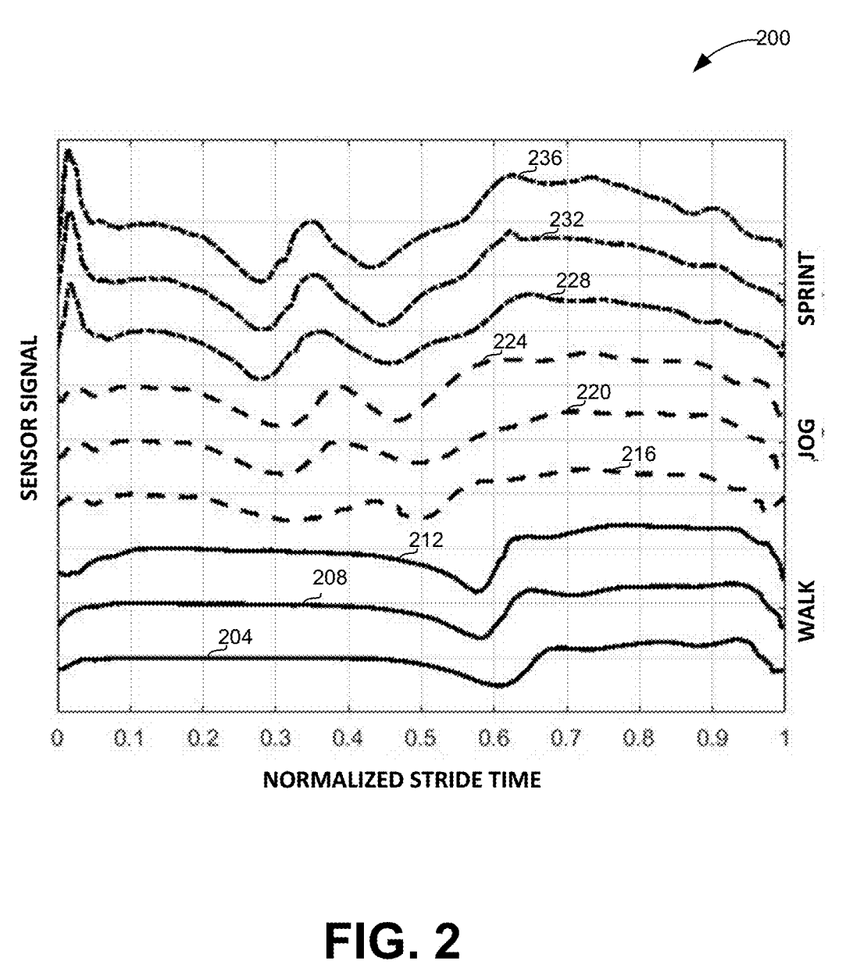
FIG. 2 shows characteristic graphs of a plurality of gait types, in accordance with some exemplary embodiments of the disclosed subject matter.

Referring now to FIG. 2, showing on graph 200 characteristic curves for a plurality of gait types.

The horizontal axis represents a normalized time of a stride, from the time the heel of one foot contacts the ground, until the same heel meets the ground again, also referred to as a double step. The vertical axis is a kinematic parameter collected during a stride, such as an angular velocity. The athlete speed increases incrementally from the lowest plot (204) to the upmost plot (236). However, graph 200 is not to scale, and the different plots are vertically shifted to allow for better visualization.

It is seen that graphs 204, 208 and 212, for which the kinematic measurements were obtained during a walking stride all have the same structure, with a pronounce variation around 0.6 of the stride time, around the time when the foot is lifted. This corresponds to the well-known walking characteristic of stance phase of taking about 65% of the stride duration.

In graphs 216, 220 and 224 for which the kinematic measurements were obtained during a jogging stride, the toe-off phase resultant structure appears at around 40% of the gait cycle, also in a good agreement with the literature. Graphs 228, 232 and 236 for which the kinematic measurements were obtained during a sprinting stride have shorter stance phase, for about 40% of the stride duration, and a much feature-intensive curvature due to the faster movements and stronger forces in the gait.

It is thus seen even with naked eyes that each gait type, such as walking, jogging and sprinting has a characteristic pattern, upon which the gate type may be identified.

Figure 3A:
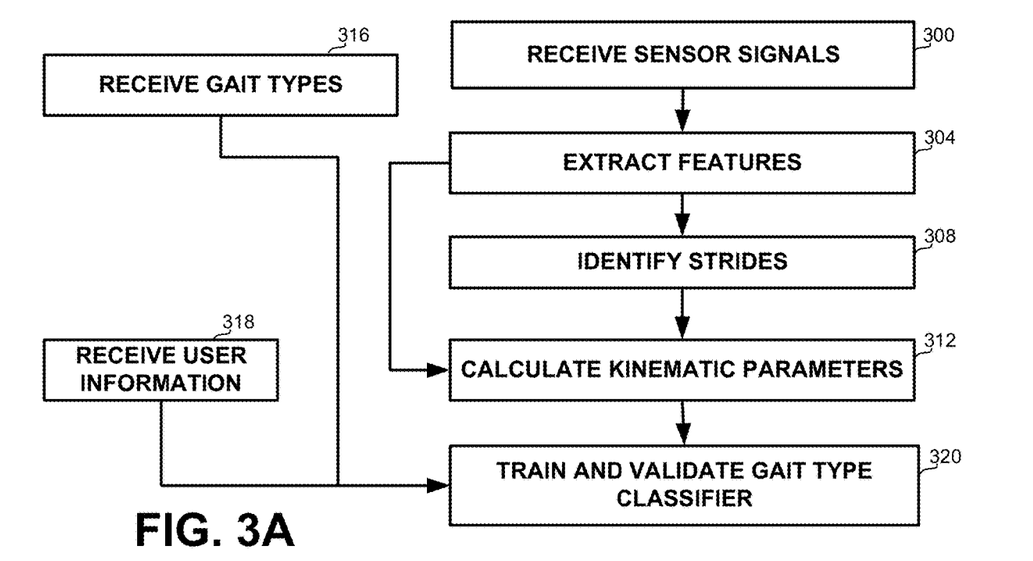
FIG. 3A, shows a flowchart of steps in a method for training a gait type classifier, in accordance with some exemplary embodiments of the disclosed subject matter.

Referring now to FIG. 3A, showing a flowchart of steps in a method for training a gait type classifier.

On step 300, sensory data such as sensor signals may be received from one or more sensors such as the IMU sensor described above worn by a subject. The data may be received directly from the sensors, or from a storage unit where the data has been collected. The signals may be provided from one sensor mounted on a subject's shoe. In some embodiments, signals may also be received from at least one additional sensor, such as a sensor mounted on the subject's other shoe, a sensor mounted on another body part of the subject such as a hand, or the like.

At least one of the sensors may be an IMU sensor as described above.

On step 304, kinematic features may be extracted for each stride or sequence of strides. The features may include but are not limited to any one or more of the following:

Sport/environment specific features, for example ball touch data during a football related activity, such as type, e.g., receive, release, or dribble, the part of the foot that touched the ball, release velocity, or the like. This information may come from different processing of data extracted from the same sensor, or from a different source, for example a different sensor carried by the user, a sensor attached to the ball, processed images, or the like.

Any features calculated from the raw sensor data extracted from the normalized stride duration and distance, which may or may not be normalized, for example to 1: maximal values of each of the sensor signal and the corresponding time, local extremums of the signal, the change of sign times of the signal as well as the standard times and frequency domain features.

Any features calculated in an axis system such as the global axis system, for example: global and local extremums of position, velocity and acceleration (normalized or not), time and frequency domain features and correlation between the axes.

Sensor raw data in at least one dimension in time or frequency domain.

Three dimensional motion profile of the subject.

On step 308, a sequence of strides may be identified within the sensory data. In some embodiments, the sequence may be computed directly, for example, a position change direction indicating that the subject's foot hit the ground may indicate a beginning of a stride. In other embodiments, indirect calculation may take place, for example thorough a learning model based on the kinematic parameters.

On step 312, kinematic parameters may be extracted from the feature values associated with each stride or sequence of strides, upon the stride type, and the extracted features for the stride. The features may include but are not limited to any one or more of the following:

Stride characteristics, such as: side, length, duration, speed, contact time with the ground, flight ratio, change in heading angle, pronation, maximal foot height, change in height for example when climbing stairs, or the like. In some embodiments, one or more features such as stride duration or stride distance may be normalized, for example to 1.

Stride characteristics of a sequence of one, two, or more strides, such as the above features for one or more preceding strides as well as acceleration, e.g., change of speed with respect to preceding and/or following strides.

On step 316, a collection of gait types may be received, into which it may be required to classify the strides. If such collection is provided, the sensory data received on step 300 may be labeled, such that the features extracted for each stride are associated with a gait type of the collection. The gait types may include but are not limited to combinations of one item from each of the following lists:

Run, walk, or jump;
Forward, backward, turn (left or right), side stepping (left or right), up, down, or same position;
Acceleration, deceleration, or constant velocity;
Environment specific parameters, for example ball related gaits: receive, release, dribble, or no touch;
Game specific motions, for example tackle.

Thus, a gait class may be for example: "Walk, forward, constant velocity, no touch" or "Run, turn, deceleration, no touch".

The class definitions may be further combined with motions types which interact with the environment, such as like dribbling with the ball during a football game. The subtle step modification due to the ball touches may be utilized to further classify the dribbling event. In another example, additional input to the data can be the actual ball touches, which due to their low power are hard to identify.

On step 318, additional data features, such as subject information may be obtained, for example height, weight, leg and foot length, age, gender, dominant leg, and medical information such as injury or neurological condition. The data may be obtained, for example from a database associating an identifier of the data with a subject.

On step 320, one or more classifiers may be trained for the one or more gait types, upon some or all the sensory data.

Some data may be used for validating the classifier rather than for training. Training may include supervised training, in which gait types are received and the training sensory data is labeled in accordance with the types.

In alternative embodiments, unsupervised training may be performed, in which the sensory data is clustered according to a distance function between collections of stride features.

In yet other alternative, a combination of supervised and unsupervised learning may be performed, for example by initially clustering some unlabeled data and further training with labeled data, or vice versa.

It will be appreciated that the more specific the stride is, i.e. the more stride types exist, the smaller and more focused is the model.

It will be appreciated that the classifier may be modified to accommodate information and base the stride classification on multiple strides, such as a previous stride, a following stride, a stride by the other leg, or the like.

In some embodiments, classification may relate to classifying a motion comprising a multiplicity of strides, rather than a single stride.

In some embodiments, classification may utilize data about specific motions which may be identified independently by the sensor, such as ball touches.

In some embodiments, classification may relate to the user phase rather than the stride phase, as determined in accordance with an additional level of modeling, such as HMM. For example, classification may be that the user is running, rather than "the stride of the left foot is a running stride".

Figure 3B:
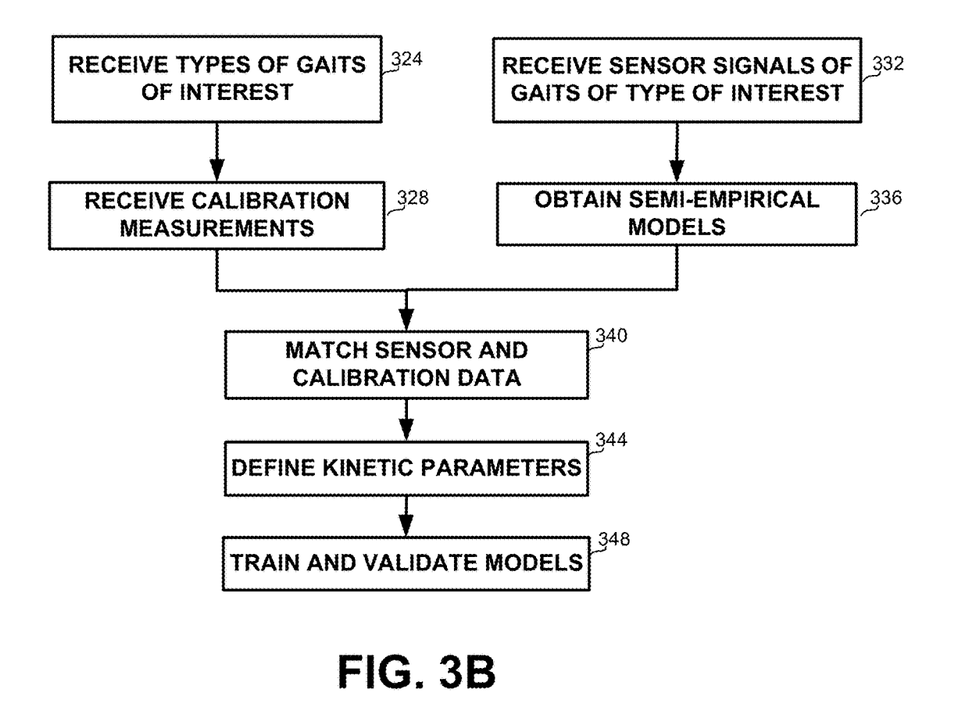
FIG. 3B shows a flowchart of steps in a method for training a model for a specific gait type, in accordance with some exemplary embodiments of the disclosed subject matter.

Referring now to FIG. 3B, showing a flowchart of steps in a method for training a kinetic model for a specific gait type.

On step 324, one or more gait types of interest may be selected or received, for example any of the gait types identified by a classifier created in accordance with the method of FIG. 3A above. The types may include gait types that tend to occur frequently in relevant activities, or of significant severance, or correlate to phenomena of interest, such as specific injuries. The specific selection of gait types may also depend on the relevancy to the kinetic parameters that would be extracted, and the natural occurrence of these gait types in the activity that would be analyzed, such as a football game, an elder person daily routine, or the like.

On step 328, calibration measurements may be received for the specific gait type(s). Calibration measurements may include data associating certain kinematic parameter combinations with the kinetic parameters. The data may be received, for example from stationary equipment in a controlled environment such as a laboratory, in which subjects perform gaits of the specific type. The calibration measurements, which comprise data related to a plurality of discrete values, may provide a starting point for a model which may then be improved. The calibration data may include, for example, electromyogram or mechanomyogram data of different muscles and force plate data of ground reaction forces.

On step 332, sensory data, comprising sensor signals of gaits of the types of interest may be received. The sensory data may be filtered from a larger collection of sensory data, as classified to the required gait types by a classifier created in accordance with the method of FIG. 3A above.

The sensory data may undergo stride identification and kinematic parameter calculation as detailed above. In some embodiments, the sensory data used for creating a classifier in accordance with the method of FIG. 3A may be re-used, such that the stride identification and kinematic parameter calculation as detailed above need not be repeated.

On step 336, a semi-empirical model may be received or calculated, which associates the kinematic parameter combinations with the corresponding kinetic parameters. Semi-empirical models may be based on assumptions, approximations, or generalizations designed to simplify calculations or to yield a result in accord with observations, thereby replacing as many calculations as possible with pre-calculated data.

During the calibration of a kinetic model, only a finite number of movements can be measured. One of the machine learning goals is to interpolate this discrete set of measurements, to be able to handle slightly different states. However, some states may not be well defined in an uncontrolled environment. Specifically, some kinematic parameters may be affected by coupling between movement of different body parts, such as feet, hips, body or the like. Therefore, "effective states" may be defined based on the movement information collected throughout an activity period. These effective states may be used to calculate the characteristic kinetic parameters, based on the trained model, during the activity for this specific gait type.

For example, some of the kinematic parameters describing the movement state are related to the difference in the ground contact time between the feet, as well as the symmetry of flight time, step length, flight time Etc. The assumption behind these parameters is that the stride speed is identical for both legs, however in an uncontrolled environment this condition may never be met. In order to define effective asymmetry, it can be assumed, instead, that the ratio between a specific stride ground contact time and the resultant speed is constant for a specific gait type, such as forward run in roughly constant speed. This ratio can be described by an analytic model in which some of the parameters predict the contact time asymmetry for each stride (which depends on its speed), for example:

$$\tau_{l,r}(v) = \tau_S \cdot e^{-(\alpha_S \pm 0.5\alpha_{AS}) \cdot (v-v_0) \pm 0.5\beta_{AS}}, \text{ wherein}$$

l and r indicate the left and right foot, respectively;
$v_0$ is a representative speed;
$\tau_S$ is a contact time at speed of $v_0$ in seconds;
$\alpha_S$ is a contact time decay in sec/meter;
$e^{\beta_{AS}}$ is a contact time asymmetry at speed of $v_0$; and
$\alpha_{AS}$ is a contact time asymmetry decay in sec/meter.

Given the semi-empirical model, when the kinetic model is used to calculate the loads during activity, the kinetic model may be applied to the effective states in which each stride at a specific speed has asymmetry parameters which are defined by the above model, for the relevant gait type. For example, the contact time asymmetry for some stride with speed of v1 is $\tau_l(v1)/\tau_r(v1) = e^{-\alpha_{AS}*(v1-v0)} \cdot e^{\beta_{AS}}$.

On step 340, the sensor data received on step 332 and the calibration data received on step 336 may be sorted and matched for each gait type.

On step 344, the relevant kinetic parameters of interest for each train type may be defined.

On step 348, a model may be trained and validated upon the sensory data, using the available calibration measurements and optionally the semi-empirical model, for the kinetic parameters of interest. The model may provide kinetic parameters for a given collection of kinematic parameters, thereby providing bio-mechanical information that may assist in improving the motion performance and training, and avoiding injury of the subject.

Due to the gait-type-wise generation of the models, the database may be constructed over time, for example starting with the few most important gait types, and proceeding with additional ones as time and budget permit.

In some embodiments, the model may be based also on one or more analytic kinetic models. For example, modeling the legs as masses and springs. An example for such model is the "two mass" model discussed by Clark, Ryan and Weyand in "A general relationship links gait mechanics and running ground reaction forces", Journal of Experimental Biology (2017) 220, 247-258, incorporated herein by reference in its entirety for all purposes. The proposed model predicts the ground reaction forces based on simple kinematical gait parameters. It can predict with some inaccuracy the characteristic GRF the athlete uses at a first speed, and thus transforms the athlete condition state from pure kinematics to kinematic parameters (forces and energies). Since this model does not support leg asymmetry properly it is insufficient, but can be combined with the machine learning methods, and thus reduce the complexity of the deep learning model.

Figure 4:
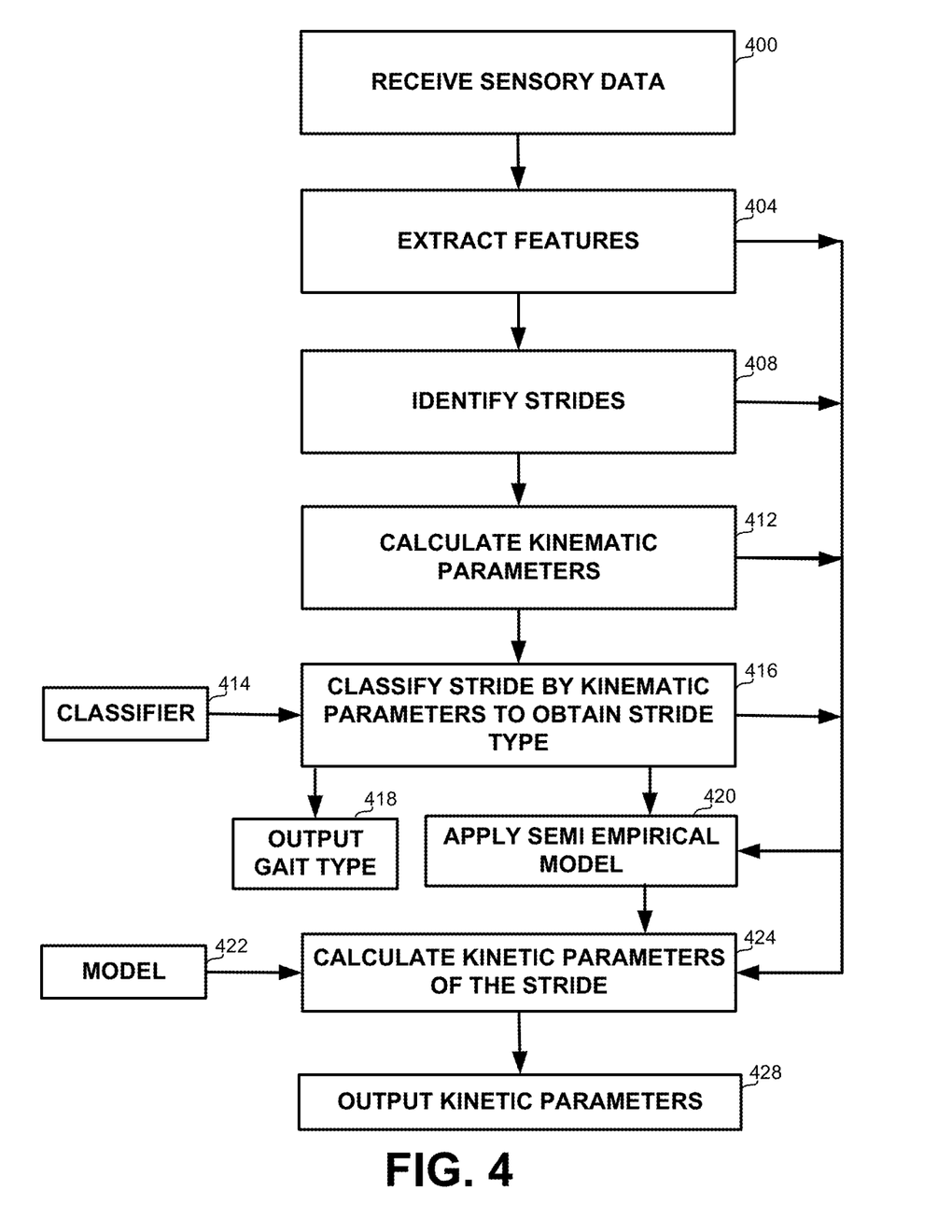
FIG. 4 shows a flowchart of steps in a method for classifying gaits and obtaining kinetic parameters of the gaits, in accordance with some exemplary embodiments of the disclosed subject matter.

Referring now to FIG. 4, showing a flowchart of steps in a method for classifying gaits and obtaining kinetic parameters of the gaits.

On step 400, sensory data may be received, as detailed in association with step 300 above. However, the data is runtime data, and is thus unlabeled.

On step 404 features may be extracted from the data, as detailed in association with step 300 above.

On step 408 data related to one or more strides may be obtained, as detailed in association with step 308 above.

On step 412 kinematic parameters may be calculated upon the data, as detailed in association with step 312 above.

On step 416, a gait type classifier 414, such as a classifier trained in association with FIG. 3A above may be obtained, and the data may be provided to the classifier. The classifier may then output a gait type that is most probable for the specific kinematic parameters of a given stride.

On step 418 the gait type into which the stride was classified may be output, for example to a storage device, to a file, displayed or read to a user such as a coach, indicated graphically or the like.

In some embodiments, further calculations may be made upon the gait types of one or more strides, for example statistical analysis of a subject, a group, or the like.

On step 420, a semi-empirical model may be applied to the collected data, to obtain an interpolation of the kinematic parameters, where the exactness of the available data is insufficient.

On step 424, a model 422 of the specific gait type may be obtained, and the data, including the interpolated data, extracted features, the identified strides, and the kinematic parameters may be provided to model 422. Model 422 may then provide an assessment of the kinetic parameters exerted by and on the subject in association with the stride. The model output can be a quantitative estimation of load(s) and combination of different parameters. The model may also include phenomenological aspects, such as quantitative data related to high/low intensity.

In some embodiments, the method may comprise comparing the kinetic and kinematic motion parameters of a subject over time, thereby obtaining indication to neurological conditions or risks, such as increased risk of fall, recognition of abnormal gait patterns, or the like. This comparison may be applied every predetermined period of time, for example every day, week, month or the like, thus providing for early detection of problematic conditions.

On step 428, the kinetic parameters may be output, for example to a storage device, to a file, displayed or read to a user such as a sport scientist or a physician, indicated graphically or the like.

In some embodiments, further calculations may be made upon the kinetic parameters of one or more strides, for example statistical analysis, estimation of injury, or the like. In some embodiments, the kinetic model may be used to obtain kinetic parameters of an entire segment. Moreover, the kinetic parameters of multiple segments may be combined to draw conclusions related to a condition, injury, performance, or the like, of a subject.

Figure 5:
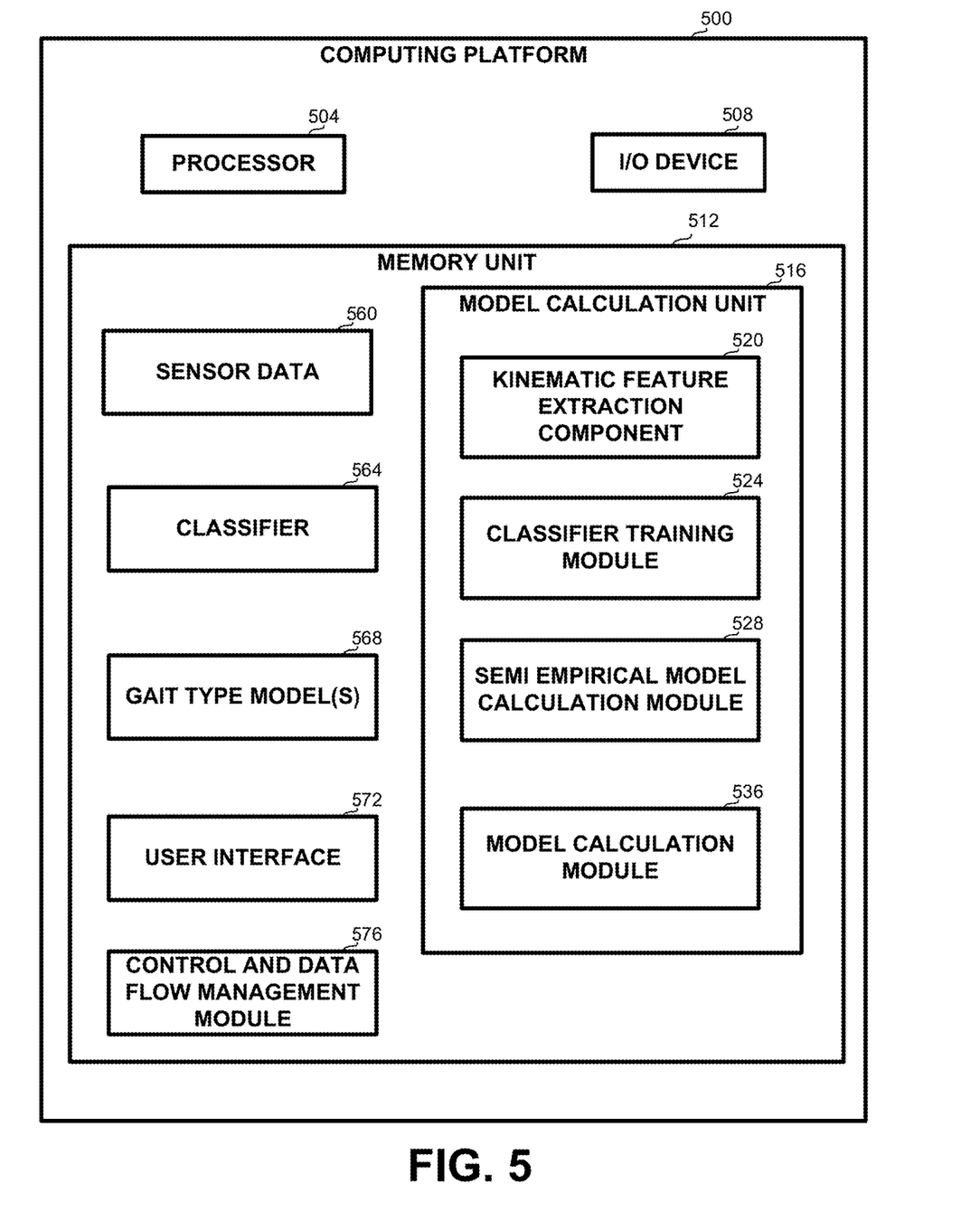
FIG. 5 is a block diagram of a computing platform 500 for obtaining kinetic parameters of motion from kinematic parameters, in accordance with some exemplary embodiments of the disclosed subject matter.

Referring now to FIG. 5, showing a block diagram of a computing platform 500 for obtaining kinetic parameters of motion from kinematic parameters, in accordance with some exemplary embodiments of the disclosed subject matter.

It will be appreciated that one or more of the components detailed below may be executed by a remote processor communicating with computing platform 500, such as a remote server. The remote server may receive information and provide results to multiple instances of computing platforms 500, whether associated with the same user, with different users acting together such as a sports team, or form unrelated users. In some embodiments, a hybrid approach may be taken, in which initial calculations are performed in real time by a computing platform embedded within the device. The calculations may then be improved by a remote computing platform, upon data received form additional sensors and/or players.

In some exemplary embodiments computing platform 500 may comprise a processor 504, which may be a Central Processing Unit (CPU), a microprocessor, an electronic circuit, an Integrated Circuit (IC) or the like. Processor 504 may be utilized to perform computations required by computing platform 500 or any of its subcomponents. Processor 504 may be configured to execute computer-programs useful in performing the method of FIGS. 3A, 3B and 4 above.

In some exemplary embodiments, one or more I/O devices 508 may be configured to receive input from and provide output to a user. In some exemplary embodiments, I/O devices 508 may be utilized to present to the user a user interface, obtain user definitions for the gait types, and display the results such as a specific classification, classification statistics, a representation of the kinetic forces acting on or applied by a subject on a specific stride or segment, statistic for a specific gait type or different gait types for a specific subject or a group of subjects, or the like. I/O devices 508 may comprise a display, a keyboard, a mouse, a touch screen or another pointing or tracking device, a voice activated device, or the like.

In some exemplary embodiments computing platform 500 may comprise a memory unit 512. Memory unit 512 may be a short-term storage device or long-term storage device. Memory unit 512 may be a persistent storage or volatile storage. Memory unit 512 may be a disk drive, a Flash disk, a Random Access Memory (RAM), a memory chip, or the like. Memory unit 512 may be a single memory device, or multiple interconnected memory devices which may be co-located or located in different locations and communicating via any communication channel.

The components detailed below may be implemented as one or more sets of interrelated computer instructions, executed for example by processor 504 or by another processor. The components may be arranged as one or more executable files, dynamic libraries, static libraries, methods, functions, services, or the like, programmed in any programming language and under any computing environment.

In some exemplary embodiments, memory unit 512 may retain program code operative to cause processor 504 to perform acts associated with any of the subcomponents of computing platform 500. In some exemplary embodiments, memory unit 512 may retain program code operative to cause processor 504 to perform acts associated with any of the steps shown in FIG. 3A, 3B or 4 above.

Memory unit 512 may retain sensory data 560 comprising readings received from one or more sensors mounted on one or more subjects.

Memory unit 512 may retain model calculation unit 516, comprising components for creating a classifier and one or more gait-type specific models, as shown in FIGS. 3A and 3B above.

Model calculation unit 516 may retain kinematic feature extraction component 520 for extracting kinematic parameters from sensory data 560. The kinematic parameters may be as disclosed in association with step 312 above.

Model calculation unit 516 may retain classifier training model 524 for receiving the kinematic parameters and generating a classifier based thereon. The classifier may be trained in supervised mode in which case the data may be labeled, unsupervised mode, or a combination thereof.

Model calculation unit 516 may retain semi empirical model calculation module 528 for determining a semi empirical model connecting between certain parameters, and comprising one or more formulae, look up tables, or the like, for relieving the constraint of performing gait analysis based only on data collected in controlled environments.

Model calculation unit 516 may retain model calculation module 532 for calculating a model transforming from the kinematic parameters to the kinetic parameters for a specific gait type, using calibration measurements and optionally a semi-empirical model.

Memory unit 512 may retain classifier 564 for classifying further sensory data, wherein the classifier may have been created by classifier training module 524.

Memory unit 512 may retain one or more gait type models 568, as may have been obtained from model calculation module 532.

Memory unit 512 may retain user interface 572 for receiving instructions or preferences from a user, and providing information to the user over I/O device 508.

Memory unit 512 may retain data and control flow management module 576 for activating and managing the control flow between the various modules, obtaining and providing the data required for each module, or the like.

Experimental Results

Results obtained using the methods and system above are presented below. Videos with training athletes wearing a sensor on each foot were synced with their sensor data. The step types were manually labeled, and a classifier was then trained to predict the stride type based on features extracted from the sensor data. The analysis was done for each sensor independently, i.e., one of the features was the leg side.

Figure 6:
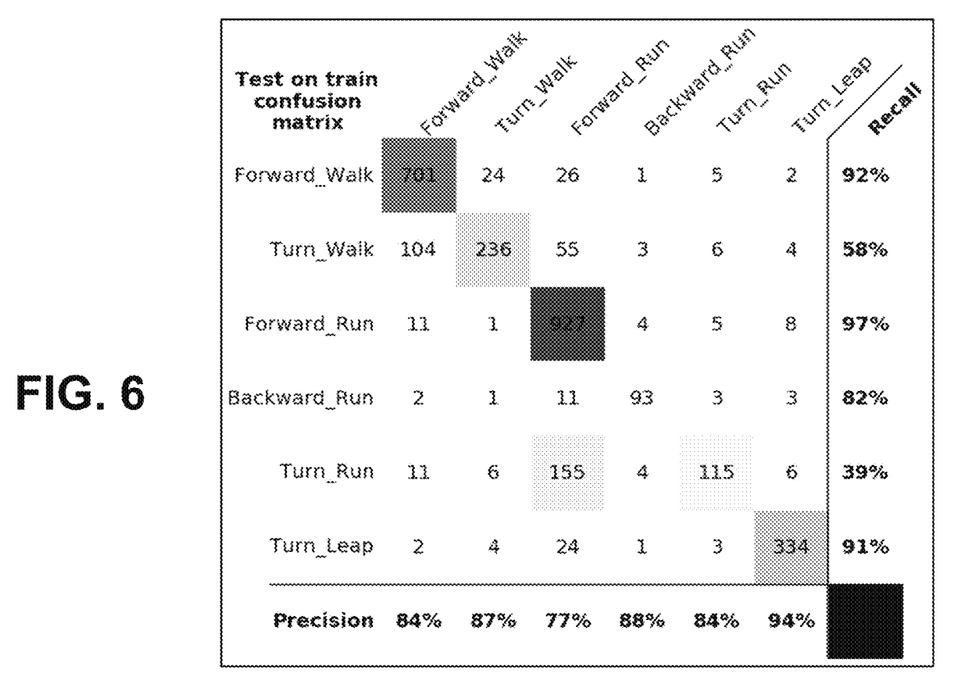
FIG. 6 is a confusion matrix of classifying a database comprising strides of six types, in accordance with some exemplary embodiments of the disclosed subject matter.

Referring now to FIG. 6, showing a confusion matrix that provides the precision and recall percentage when classifying a database comprising strides of six types. As seen, the recall percentage can be over 90% for some stride types, but can be significantly lower in other types, especially similar types. For example, the confusion may be due to the difficulty in deciding when exactly a motion changed. Thus, there is significant confusion between a forward walk and a turn walk, or between a turn run and a forward run.

The precision percentage is generally high, and does not fall below 77%.

Figure 7:
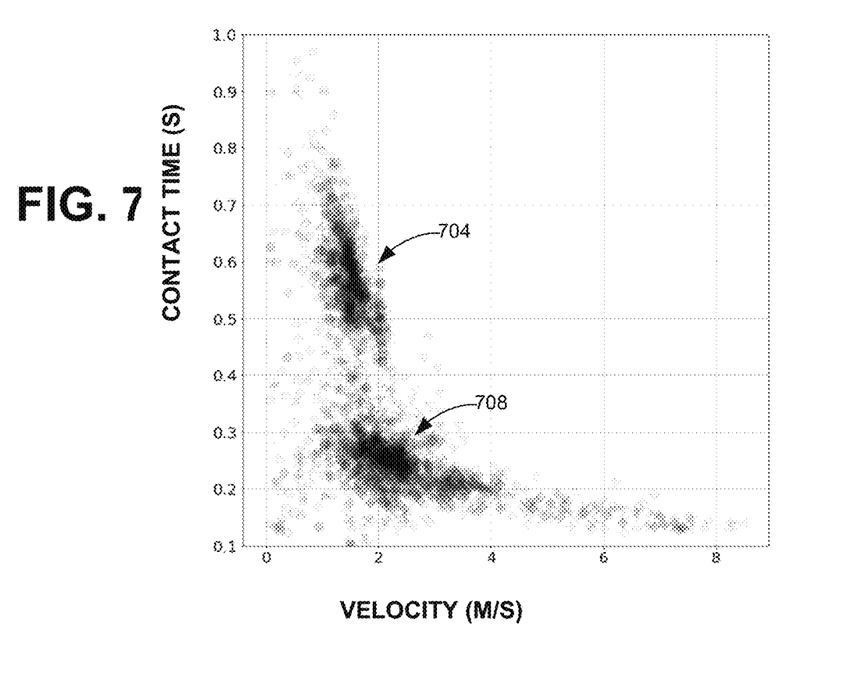
FIG. 7 is a graph of the foot on ground time vs. velocity in a gait kinematic database, in accordance with some exemplary embodiments of the disclosed subject matter.

Referring now to FIG. 7, showing a graph of the foot on ground time vs. velocity, wherein each spot indicates a value combination of a specific stride.

The results shown in FIG. 7 demonstrate the occurrences of strides according to the values of two different gait kinematic parameters as axes, being foot on ground duration (vertical axis) and velocity (horizontal axis). Each stride shape is associated with one stride type mentioned in the matrix of FIG. 6, for example a point associated with a walking stride is marked by a circle and a point associated with a running stride is marked by a cross. Multiple clusters are seen, including two significant clusters, cluster 704 indicating lower velocity and longer foot on ground times, which are typical of walking, and cluster 708 indicating higher velocity, for example 2-8 meter per second, and shorter foot on ground times, which are typical of running, wherein the stride types associated with these two clusters are consistent with the dominant types on the diagonal of the confusion matrix, being forward_walk and forward_run. Thus, FIG. 7 shows that the two kinematic parameters, being the velocity and the ground contact time, can provide a visual representation of a known behavior, as also demonstrated by FIG. 6, by showing two frequent and significant stride types, being walking and running.

Figure 8:
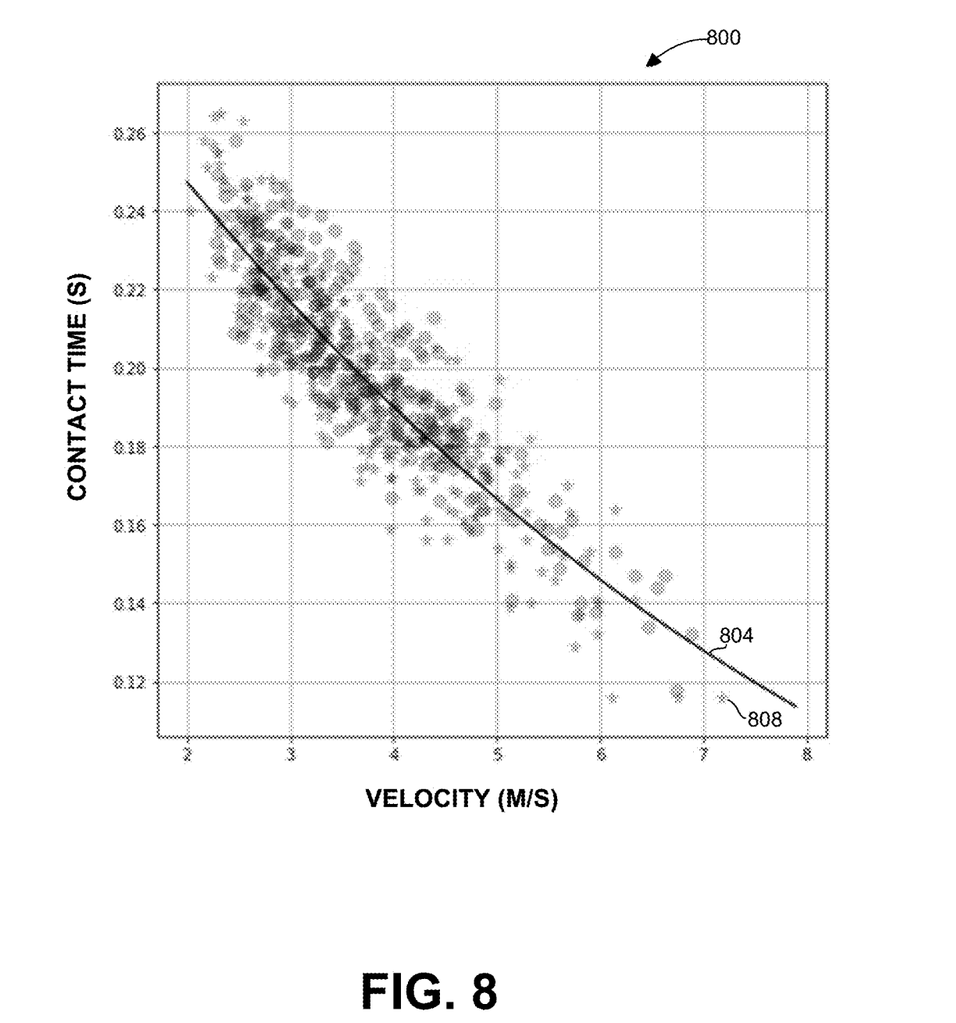
FIG. 8 is a graph of the contact time vs. velocity for the left and right foot, in accordance with some exemplary embodiments of the disclosed subject matter.

Referring now to FIG. 8 showing a graph 800 which is similar to a zoom-in of the lower right side of FIG. 7, including only straight-line running strides. The circles represent measurements for the left foot, and the starts represent measurements for the right foot, wherein each spot indicates a value combination of velocity and ground contact time for a specific stride. Curve 804 shows the behavior of the left foot, and it is seen that there is no full match between the left and the right foot. For example, while there is a left foot measurement for point 808 associated with velocity of about 7.2, there is no corresponding point for the right foot. The semi-empirical model may become useful on such situations, by providing an assessment to the right foot contact time for this velocity, based on data available for the left foot.

The dependency of the contact duration on the velocity value was used for determining the semi-empirical model including the formula disclosed above:

$$\tau_{l,r}(v) = \tau_S \cdot e^{-(\alpha S \pm 0.5\alpha_{AS}) \cdot (v - v_0) \pm 0.5\beta_{AS}}$$

Using this formula, the athlete condition from all velocities can be summarized using few parameters, thereby defining an "effective state". The formula enables measurement in uncontrolled environment, in which it is not required to run exactly at speed $v_0$, and reduces the noise coming from the variations between the strides, and is thereby useful in estimating the kinetic parameters from kinematic parameters even in the absence of the exact values in the model.

For example, using the formula it is possible to couple an effective left foot contact time to the right foot stride marked in 808. Graphically, it is done by projecting 808 on curve 804.

Figure 9:
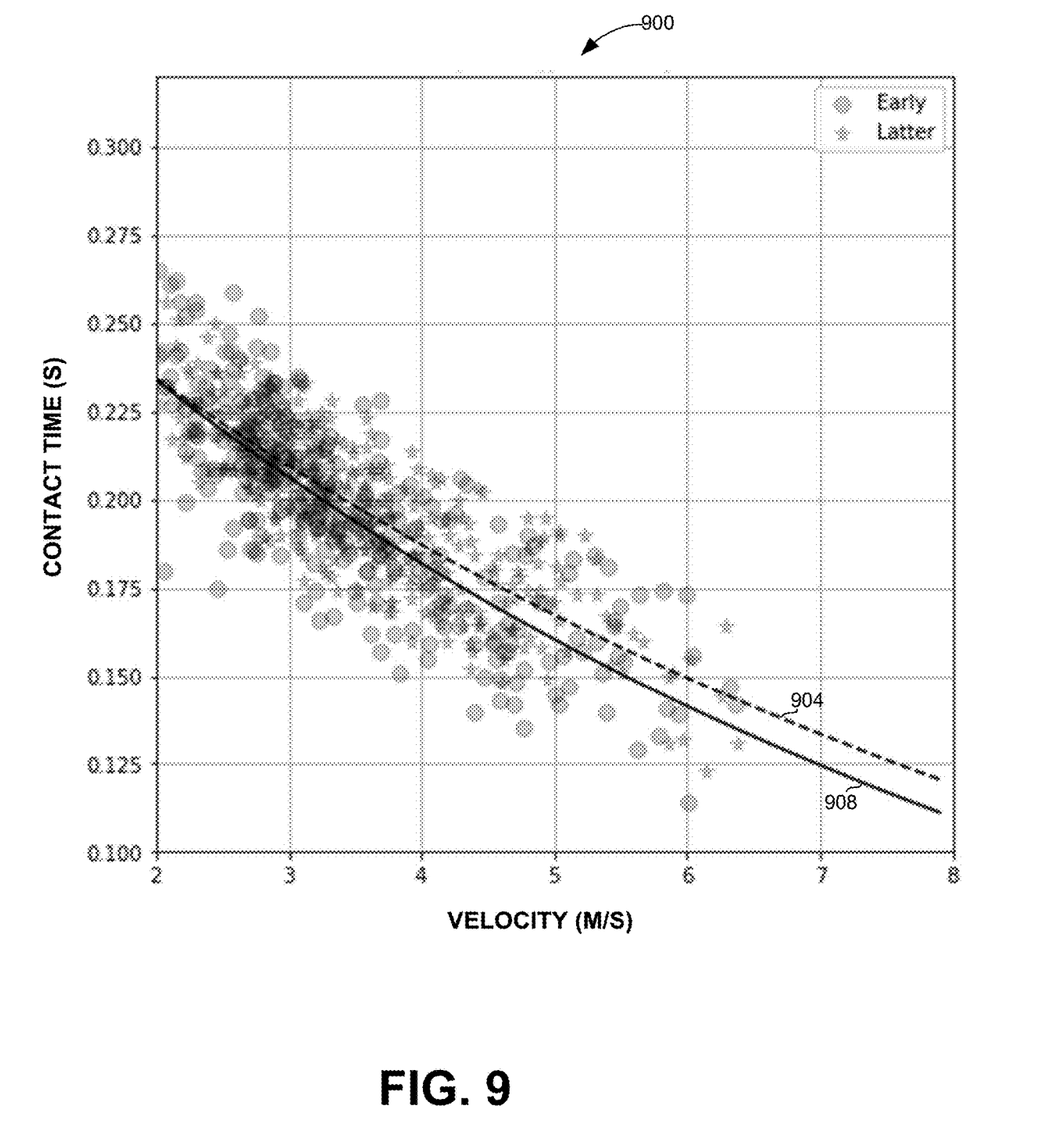
FIG. 9 is a graph of the contact time vs. velocity before and after the fatigue effect, in accordance with some exemplary embodiments of the disclosed subject matter.

Referring now to FIG. 9, showing a graph 900 of the contact time vs. velocity, wherein each spot indicates a value combination of a specific stride. Curve 908 shows early results, taken before significant effort, while curve 904 shows the results post the effort. In this case a fatigue effect can be quantified: the user had longer ground contact time at the later phase of the recording while running at the same speed. This graph shows the different comparisons that may be taken for parameters of a subject: left vs. right foot, pre or post effort, comparing on continuous basis to obtain changes over time, or the like.

Another method for quantifying the fatigue effect using this model may be to define the model based on long activity and the then look at the difference between shorter activity segments and this characteristic behavior.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as Python, MATLAB, the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method performed by a processor, the method comprising:
   receiving sensory data of motion by a human subject, the sensory data obtained during motion in an uncontrolled environment;
   extracting features from the sensory data;
   identifying a plurality of strides from the features extracted from the sensory data;
   calculating kinematic parameters of each stride from the plurality of strides from the sensory data;
   classifying each stride from the plurality of strides in accordance with the kinematic parameters to obtain a stride type, using a model associating the kinematic parameters with stride type, the model combined with an analytic model for determining effective kinematic states in the uncontrolled environment to fit to controlled environment states; and
   outputting the stride type for the plurality of strides.

2. The method of claim 1, further comprising:
   providing the kinematic parameters to a second model associating kinematic parameters and kinetic parameters for the type of gait, for obtaining kinetic forces applied on and by the human subject in response to performing gaits having the kinematic parameters; and
   outputting the kinetic parameters.

3. The method of claim 2, further comprising:
   combining kinetic parameters of multiple segments to obtain advanced kinetic parameters for a plurality of strides; and
   outputting the advanced kinetic parameters.

4. The method of claim 1, wherein at least one feature from the features is selected from the group consisting of: human subject information including: subject height, weight, age, gender, leg length, foot length, or dominant leg; stride information for each stride in a sequence of one or more strides including: side, stride length, stride duration, contact time with the ground, flight ratio, stride change in heading angle, pronation, maximal foot height, or change in height; and ball touch data, including: type or release velocity.

5. The method of claim 1, wherein at least one feature from the features relates to the sensory data in at least one dimension in time or frequency domain.

6. The method of claim 1, wherein at least one feature from the features relates to a three dimensional motion profile of the human subject.

7. The method of claim 1, further comprising combining the model with a second analytic model, for interpolating kinematic gait properties as a function of foot velocity.

8. The method of claim 1, wherein the sensory data is obtained from at least one sensor mounted on at least one shoe of the human subject.

9. The method of claim 1, wherein the sensory data is obtained from sensors mounted on at least one shoe of the subject and an additional sensor mounted on another location on the human subject.

10. The method of claim 1, wherein the sensory data is obtained from at least one sensor comprising at least one Inertial Measurement Unit (IMU) or a motion capture system.

11. The method of claim 1, wherein the method is used for assessing a medical condition of the human subject.

12. The method of claim 1, further comprising providing an indication to an increased risk of fall or another neurological condition of the human subject based on changes in kinetic and kinematic parameters or recognition of abnormal gait patterns.

13. A method performed by a processor, the method comprising:
receiving calibration measurements for a gait type, the calibration measurements providing estimations of kinetic parameters applied by a person performing actions associated with kinematic measurements;
receiving training sensory data comprising training kinematic parameters acquired from a human subject performing multiplicity of gaits of the gait type, the training sensory data obtained during motion in an uncontrolled environment;
extracting training features from the training sensory data; and
generating a model based on the training features and the calibration measurements, the model providing an estimation of kinetic parameters in response to inputting sensory data obtained during performance of a gait of the gait type.

14. The method of claim 13, wherein the calibration measurements are obtained from a device used by the person in a controlled environment.

15. The method of claim 13, wherein the calibration measurements comprise measurement data for discrete values of kinematic parameters.

16. The method of claim 13, further comprising receiving a semi empirical model associating the training kinematic parameters with training kinetic parameters.

17. The method of claim 13, wherein the model is further adapted to provide an estimation of kinetic parameters of a motion segment by a human subject.

18. The method of claim 13, wherein the gait types and the kinetic parameters for which the model is generated are selected based on frequency or severance.

19. The method of claim 13, wherein the model is also based on at least one analytic kinetic model.

20. A non-transitory computer-readable medium storing instructions that when executed by a processor causes the processor to perform a method comprising:
receiving sensory data of motion by a human subject, the sensory data obtained during motion in an uncontrolled environment;
extracting features from the sensory data;
identifying a plurality of strides from the features extracted from the sensory data;
calculating kinematic parameters of each stride from the plurality of strides from the sensory data;
classifying each stride from the plurality of strides in accordance with the kinematic parameters to obtain a stride type, using a model associating the kinematic parameters with stride type, the model combined with an analytic model for determining effective kinematic states in the uncontrolled environment to fit to controlled environment states; and
outputting the stride type for the plurality of strides.

21. The non-transitory computer-readable medium of claim 20, wherein the method further comprises:
providing the kinematic parameters to a second model associating kinematic parameters and kinetic parameters for the type of gait, for obtaining kinetic forces applied on and by the human subject in response to performing gaits having the kinematic parameters; and
outputting the kinetic parameters.

* * * * *